(12) United States Patent
Marie et al.

(10) Patent No.: US 6,848,826 B2
(45) Date of Patent: Feb. 1, 2005

(54) MAMMOGRAPHY APPARATUS AND METHOD

(75) Inventors: Alain Marie, Clamart (FR); Serge Louis Muller, Guyancourt (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 125 days.

(21) Appl. No.: 10/033,868

(22) Filed: Dec. 19, 2001

(65) Prior Publication Data

US 2002/0122533 A1 Sep. 5, 2002

(30) Foreign Application Priority Data

Dec. 19, 2000 (FR) ............................................ 00 16582

(51) Int. Cl.[7] ............................. A61B 6/04; H05G 1/02
(52) U.S. Cl. ......................................... 378/196; 378/37
(58) Field of Search ......................... 378/37, 167, 177, 378/179, 193, 195, 196, 197, 198

(56) References Cited

U.S. PATENT DOCUMENTS

| | | | |
|---|---|---|---|
| 4,979,196 A | * 12/1990 | Lieutaud et al. | ............... 378/37 |
| 5,018,176 A | * 5/1991 | Romeas et al. | ................ 378/37 |
| 5,305,365 A | 4/1994 | Coe | ............................. 378/37 |
| 5,386,447 A | * 1/1995 | Siczek | .......................... 378/37 |
| 5,938,613 A | * 8/1999 | Shmulewitz | ................. 600/461 |
| 6,607,489 B2 | * 8/2003 | Hoctor et al. | ................ 600/443 |
| 6,714,621 B2 | * 3/2004 | Rick et al. | ................ 378/98.12 |
| 2002/0003861 A1 | * 1/2002 | Rick et al. | ................ 378/98.12 |
| 2002/0122533 A1 | * 9/2002 | Marie et al. | ................. 378/196 |
| 2003/0006387 A1 | * 1/2003 | Marie et al. | ................. 250/581 |
| 2003/0076923 A1 | * 4/2003 | Andreasson et al. | .......... 378/37 |

FOREIGN PATENT DOCUMENTS

EP          0323327          7/1989

* cited by examiner

Primary Examiner—Eric S. McCall
(74) Attorney, Agent, or Firm—Cantor Colburn LLP

(57) ABSTRACT

A mammography apparatus has an examination arm with a radiation delivery head and an image receiver. The examination arm is mounted for iso-centric rotation in a plane. A support for the arm and a support column on which the support is mounted allow the height of this plane to be adjusted. Patients can be examined in the standing, leaning, sitting or laying position while in each case maintaining the axis of rotation of the examination arm on the axis of the (compressed) breast to be examined.

20 Claims, 2 Drawing Sheets

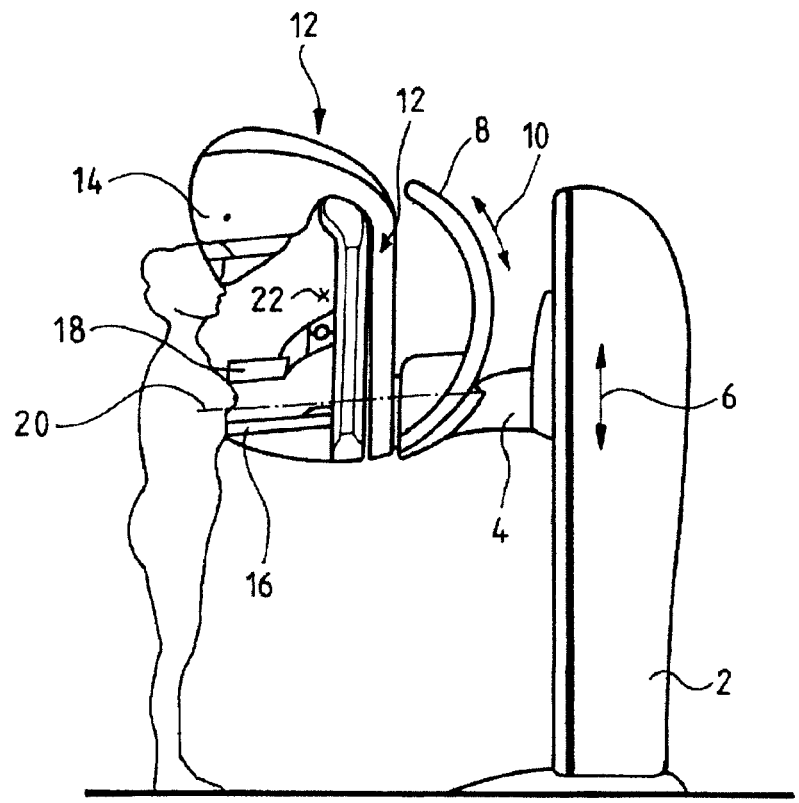
FIG_1
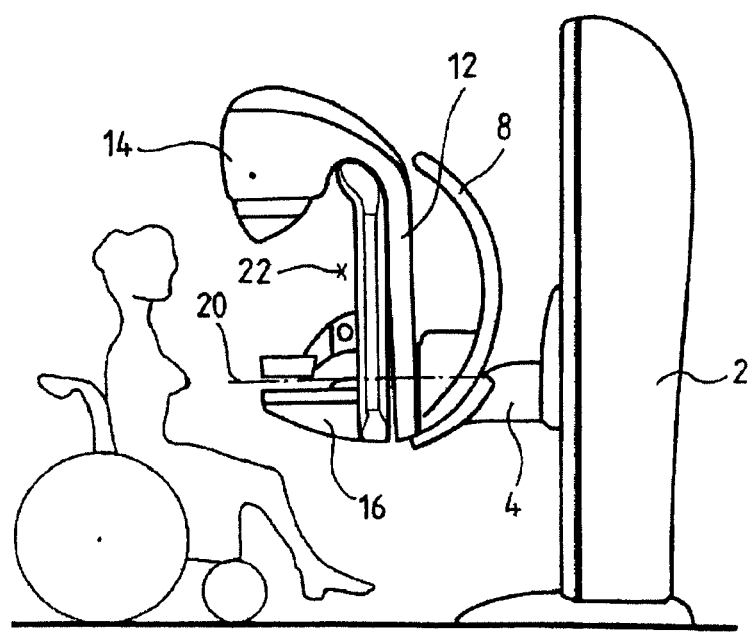
FIG_2

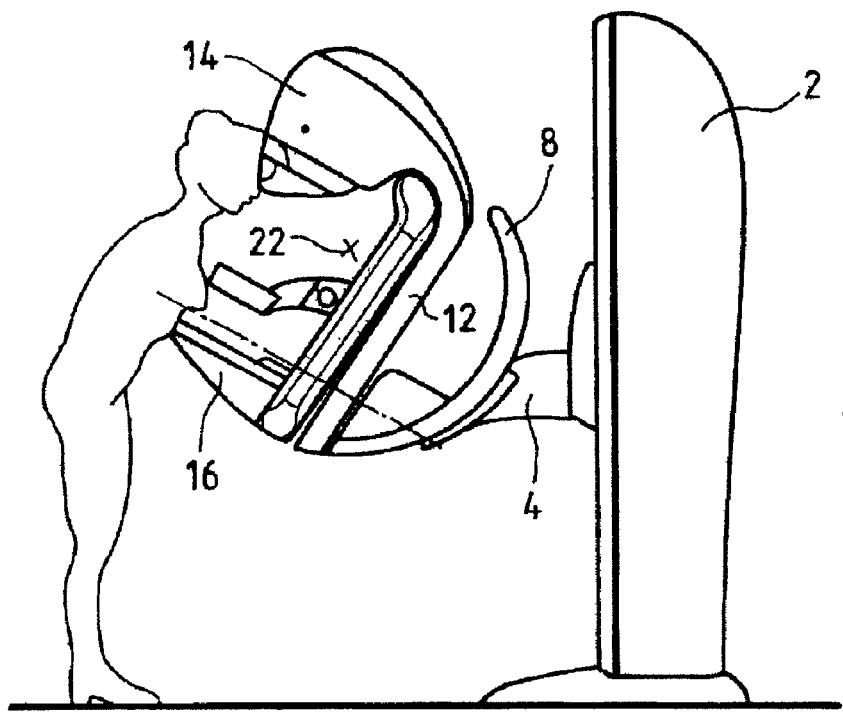
FIG_3
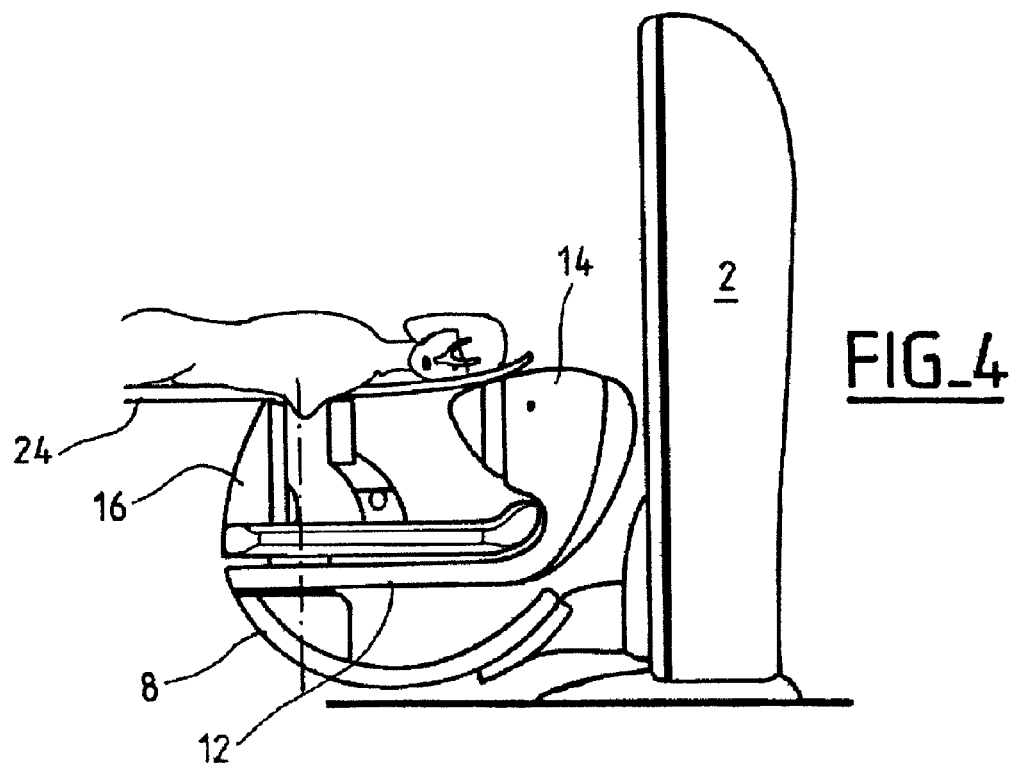
FIG_4

MAMMOGRAPHY APPARATUS AND METHOD

CROSS REFERENCE TO RELATED APPLICATIONS

This application claims the benefit of a priority under 35 USC 119 to French Patent Application No. 00 16582 filed Dec. 19, 2000, the entire contents of which are incorporated by reference.

FIELD OF THE INVENTION

The invention relates to mammography apparatus.

BACKGROUND OF THE INVENTION

Mammography systems are used for carrying out breast examination of patients using X-rays. An image is acquired using an image receiver which is either a photographic plate or digital sensing means. Such systems are used for taking cranio-caudal and lateral views. A cranio-caudal image comprises irradiating the breast from above so as to obtain a view thereof in an axis running from the head to the feet of the patient. When taking a lateral view, the breast is irradiated from the side in order to obtain a view thereof in an axis passing through the patient's body. Existing mammographs provide various positions for obtaining such views: the patient may be in a sitting, standing, forward leaning or prone position. The prone position is preferred for examinations that also involve a biopsy.

The Italian company IMS Srl is selling a mammograph under the name Ghiotto Hi-Tech which can be used for examinations in the standing or leaning positions as well as for examinations in the prone position. In the prone position, the unit is supplemented by a specialized table. The equipment comprises a crown inside of which an X-ray delivery head and image receiver are rotatively mounted. The delivery head contains those elements necessary for delivering X-rays: source, collimator, filters, etc. The image receiver is associated with a system for compressing or mechanically maintaining the organ to be examined in position. The delivery head and image receiver are located at diametrically opposite points on the crown. The delivery head and image receiver may simultaneously rotate on the crown: they consequently rotate in the plane of the crown about an axis perpendicular to the latter plane, passing through the center of the crown. The crown itself pivots about a horizontal axis passing through one of its diameters. For examination in the standing or leaning position, the crown is in a vertical or oblique plane. When it is desired to take a cranio-caudal image, the delivery head is located at the top of the crown and the image receiver at the bottom. When taking a side view, the crown is rotated so that the delivery head is at the side of the crown. For examination in the prone position, the crown is in a horizontal plane. When taking a cranio-caudal image, the delivery head is located on an axis of extension of the patient's body. To take a side view, the crown is rotated so that the delivery head is at the side of the patient. The disadvantage of this system is that it is necessary to change the patient's position when switching from a cranio-caudal image to a side view. Indeed, rotation by one quarter of a revolution of the crown causes the image receiver to change position on the crown. Access to the patient is also rendered difficult by the presence of the crown.

BRIEF DESCRIPTION OF THE INVENTION

There is consequently a need for mammography apparatus which allows, in a simple manner, varied imaging to be taken in different positions of the patient without the need to systematically move the patient or readjust the apparatus.

Briefly, in an embodiment of the present invention, the radiographic apparatus has an examination arm provided with a radiation delivery head and an image receiver. The arm is rotatively mounted on a support about a first axis of rotation, allowing an iso-centric examination. Switch-over from a cranio-caudal image to a side view (or vice-versa) is performed without moving the organ to be examined. The examination arm is also rotatively mounted on the support, about a second axis which is horizontal to and parallel with the plane in which the examination arm moves. The support is movable vertically on the support column of the apparatus.

BRIEF DESCRIPTION OF THE DRAWINGS

FIG. 1 is a diagrammatic side view of the mammography apparatus configured for examination in a standing position;

FIG. 2 is a diagrammatic side view of the apparatus in FIG. 1 configured for examination in a sitting position;

FIG. 3 is a diagrammatic side view of the apparatus in FIG. 1, configured for examination in a leaning position; and FIG. 4 is a diagrammatic side view of the apparatus in FIG. 1, configured for examination in a prone position.

DETAILED DESCRIPTION OF THE INVENTION

The mammograph will be described with reference to the drawings according to one embodiment of the invention, in various examination configurations. In addition to the apparatus, an outline of a patient is shown in lighter lines on the drawings. FIG. 1 is a diagrammatic side view of the apparatus in a configuration allowing examination in a standing position for cranio-caudal imaging. The apparatus has a support column 2 and a support 4 mounted on this support column, for translatory movement on a vertical axis. The translatory movement of the support is shown diagrammatically on FIG. 1 by arrow 6. The translatory movement of the support is also visible when FIGS. 1 and 2 are compared. In FIG. 1, the support is in an upper position with respect to the support column, for examining the patient in a standing position. In FIG. 2, the support is in a lower position with respect to the support column, for examination in a sitting position.

A C-shaped arm is mounted on the support. The C-shaped arm is in the form of an arc of a circle 8 and slides in the support 4. The resulting movement of the C-shaped arm is a motion that is shown diagrammatically on FIG. 1 by arrow 10; it is a rotary movement about an axis perpendicular to the plane of the C-shaped arm 8 with the axis of rotation passing through the center of the circle and arm 8 constituting an arc thereof. The C-shaped arm is in the vertical plane whereby its axis of rotation is horizontal. In FIG. 1, the axis of rotation is perpendicular to the plane of the drawing and is represented diagrammatically by the cross 22 on FIG. 1.

An examination arm 12 is mounted on the C-shaped arm 8. The examination arm has a delivery head 14 at one end thereof. The delivery head contains the necessary elements for delivering X-rays. The arm has an image receiver 16 at its other end. A compression pad 18 is slidably mounted on the arm, in the direction of propagation of the X-rays. The compression pad allows the practitioner who is performing the examination to compress or maintain the breast during examination. Examination arm 12 is rotatively mounted on the C-shaped arm about an axis 20 in FIG. 1. Axis 20 is substantially perpendicular to the direction of propagation of the X-rays. As shown, axis 20 is close to image receiver 16. The distance between image receiver 16 and axis 20 substantially corresponds to half of the mean thickness of the compressed breast of a patient. Thus, the axis of rotation of the examination arm passes through the center of the examination position intended for the patient's breast. This configuration of the apparatus obviates the need to modify the position of the support on the support column when changing over from taking a cranio-caudal image to side views or other views. Rotation of the examination arm about axis 20 enables the angle at which the image is taken to be modified without it being necessary to move the patient or the examination head. The shape of examination arm 12 ensures ready access to the patient by the practitioner, from either side.

The apparatus in FIG. 1 for taking a image in the standing position of the patient is as follows. First, the C-shaped arm 8 is moved so that rotation axis 20 of the examination arm 12 is substantially horizontal, as shown in FIG. 1. The vertical position of the examination arm can now be set by moving support 4 up or down on support column 2. The assembly comprising the examination arm 12 and the C-shaped arm 8 moves vertically to reach the position shown in FIG. 1. In this position, the image receiver is just below the patient's breast and rotation axis 20 of the examination arm 12 is substantially aligned with the patient's breast. The position of support 4 on the support column and the angular position of examination arm 12, rotating about axis 22 are consequently set. This sets the plane in which examination arm 12 will move during rotation about axis 20. In FIG. 1, this plane is vertical.

Cranio-caudal images can now be taken once the patient has been positioned. To change the image, it is sufficient to release the patient and then rotate the examination arm 12 about axis 20 without the need for the C-shaped arm 8 or the support 4 to be moved. As the examination arm is iso-centric, rotation of the examination arm 12 gives an identical examination position for the patient's breast. It is sufficient to again position the patient to take the image. It is not necessary, when taking an image other than the one shown being taken on FIG. 1, to move the C-shaped arm 8 or the support 4. The apparatus is consequently simple to use, fast and accurate. Adjusting the apparatus to adapt it to the size or position of the patient is done once-and-for-all. Once this is done, the configuration of the apparatus is only modified as a function of the angle at which the image will be taken at.

FIG. 2 is a diagrammatic side view of the apparatus in a configuration for taking images in a sitting position, for cranio-caudal views. The elements and features already described with reference to FIG. 1 will be seen again on FIG. 2. In FIG. 2 the difference is that support 4 is at a lower position on support column 2 whereby the axis of rotation 20 of the examination arm is lower than in FIG. 1 and is at the level of the sitting patients's breast, as shown. Like FIG. 1, to take other images, it is sufficient to rotate the examination arm 12 without modifying the position of the C-shaped arm 8 or the support.

FIG. 3 is a diagrammatic side view of the apparatus in FIG. 1, in a configuration for examination in a forward leaning position. The configuration shown in FIG. 3 differs from that in FIG. 1 in that support 4 is positioned slightly lower, while the C-shaped arm 8 has been rotated through about 30°. In this way, the examination arm 12 rotates in a plane which is inclined by about 30° with respect to the vertical.

For taking images in the leaning position of FIG. 3, the apparatus operates as follows. First, the C-shaped arm 8 is moved so that the axis of rotation 20 of the examination arm 12 is inclined by about 30° with respect to the horizontal, as shown in FIG. 3. Next, the vertical position of the examination arm 12 is adjusted by moving support 4 on support column 2. The assembly comprising the examination arm and the C-shaped arm 8 moves vertically to reach the position shown in FIG. 3. In this position the image receiver is just below the patient's breast and the axis of rotation of the examination arm 12 is substantially aligned with the patient's breast. The patient can rest against the examination arm 12 for taking cranio-caudal images. To change the view, it is sufficient to rotate the examination arm 12 about axis 20 without any need to shift the C-shaped arm 8 or the support 4. As the examination arm is iso-centric, rotating the examination arm 12 leads to a position where the image can be taken without any need to move the patient. It is not necessary, when taking an image other than the one shown being taken on FIG. 3, to move the C-shaped 8 arm or the support 4. The apparatus is consequently simple to use, fast and accurate.

FIG. 4 is a diagrammatic side view of the apparatus in FIG. 1, in a configuration for examination in the prone position. In this configuration of the apparatus, the C-shaped arm 8 has been moved on its support so that rotation of the examination arm 12 is vertical. Support 4 is lowered on the support column so that the C-shaped arm is as low as possible. The patient is laying on a table 24 with an opening for the breast arranged above the axis of rotation of the examination arm. Again, like the configurations in FIGS. 1–3, it is not necessary to move the patient or table 24 on which the patient is lying to take different images.

The apparatus thus makes it possible to take images in all possible positions of the patient. Further, it allows different images to be taken with minimal adjustment of the apparatus. Indeed, adjustment of the position of the plane defined by rotation of examination arm 12 about axis 20 is set at the outset. This adjustment is not modified for different angles of view.

This apparatus has the following advantages. Regardless of the patient's position, the apparatus allows a changeover from taking a cranio-caudal image to a side view without moving the examination position of the breast. As the support can move vertically on the support column, the apparatus allows examination in the standing or the sitting position. Because of the possibility of rotation about the second axis, the apparatus also allows examination in a leaning or even a prone position. Finally, the presence of the examination arm permits the patient to remain readily accessible to the practitioner who is operating the apparatus. The apparatus thus makes it possible to take all images in all positions, without involving any change of equipment.

The following is the various dimensional characteristics of the apparatus in FIGS. 1–4. The height of the support column depends on examination height for standing patients; in the lowest position of support 4 shown on FIG. 4, the apparatus is adapted to patients in the laying position. In the highest position of support 4 shown in FIG. 1, the support is substantially level with the breast of a standing patient. The vertical travel of the support consequently depends on the maximum height of patients to be examined and, more precisely, on a maximum height with respect to the floor of the patient's breasts. The C-shaped arm is dimensioned to allow the examination arm to operate in a vertical plane, as shown in FIG. 1, and in a horizontal plane, as shown in FIG. 4. The C-shaped arm typically extends over an arc of a circle with a central angle of 90°, i.e., one quarter of a revolution. This value makes it possible to change from a vertical position to the horizontal position. The size of the C-shaped arm, in other words, the radius of a circle of which the arm constitutes an arc, depends on the size of the examination arm. As shown in FIG. 4 the C-shaped arm is sufficiently large to allow free travel of the examination arm in all possible inclinations. The size of the examination arm depends on criteria known per se, notably the size of image receiver 16 and the irradiation capabilities of the source. Rotation of the examination arm about axis 20 is advantageously sufficient to allow at least cranio-caudal and side view images to be taken of the left- and right-hand breasts. A 180° travel both sides of the vertical position of the examination arm is sufficient. A greater degree of travel allows inclined images to be taken with the examination head lower than the breast to be viewed.

Instead of the C-shaped arm, a system of swivel joints could be used allowing the examination arm to pivot about an axis perpendicular to the plane of FIG. 1. The advantage of using the C-shaped arm as described in the examples is to enable more compact apparatus to be provided. A swivel joint on the base of the examination arm would require a long support 4, to allow a changeover to the laying position of FIG. 4. A swivel joint on the top part of the examination arm 4 would allow a support of the same type as that shown in the drawings to be used but, in this case, support column 2 has a greater length to allow the changeover to the standing position of FIG. 1.

Various modifications in structure and/or steps and/or function may be made by one skilled in the art without departing from the scope and extent of the invention as recited in the claims.

What is claimed is:

1. An apparatus comprising:
    an examination arm with, at one end thereof, an image receiver, and a radiation delivery head at the other end,
    a support on which the arm is mounted;
    the arm being mounted for rotation about a first axis substantially perpendicular to the direction of the examination arm and passing through the center of an examination position intended for an object to be examined, such that a switch-over from a cranio-caudal image to a side view image may result from rotation of the examination arm about the first axis with the object to be examined substantially stationary;
    the arm being further mounted for rotation about a second axis substantially perpendicular to the first axis and to the examination arm, the second axis being disposed between the one end and the other end of the examination arm; and
    a support column on which the support can be moved up and down vertically.

2. The apparatus of claim 1 wherein the examination arm is mounted on a support for rotation about the second axis via a C-shaped arm.

3. The apparatus of claim 1 wherein the examination arm is mounted for rotation about the second axis with a range of angular travel varying from a vertical position to a horizontal position.

4. The apparatus of claim 2 wherein the examination arm is mounted for rotation about the second axis with a range of angular travel varying from a vertical position to a horizontal position.

5. The apparatus of claim 1 wherein the examination arm is mounted for rotation about the first axis with a range of angular travel greater than or equal to 180° at both sides of a vertical position of the examination arm.

6. The apparatus of claim 2 wherein the examination arm is mounted for rotation about the first axis with a range of angular travel greater than or equal to 180° at both sides of a vertical position of the examination arm.

7. The apparatus of claim 3 wherein the examination arm is mounted for rotation about the first axis with a range of angular travel greater than or equal to 180° at both sides of a vertical position of the examination arm.

8. A method for taking images of an object with an apparatus comprising:
    an examination arm with, at one end thereof, an image receiver and a radiation delivery head at the other end;
    a support on which the arm is mounted the arm being mounted for rotation about a first axis substantially perpendicular to the direction of the examination arm and passing through the center of an examination position intended for an object to be examined, such that a switch-over from a cranio-caudal image to a side view image may result from rotation of the examination arm about the first axis with the object to be examined substantially stationary;
    the arm being further mounted for rotation about a second axis substantially perpendicular to the first axis and to the examination arm, the second axis being disposed between the one end and the other end of the examination arm;
    a support column on which the support can be moved up and down vertically;
    comprising the steps of;
    adjusting the position of the support on the support column and the angular position of the examination arm about the second axis;
    adjusting the angular position of the examination arm about the first axis; and positioning the object and taking the images.

9. The method of claim 8 comprising the steps of:
    releasing the object;
    changing the angular position of the support arm about the first axis; and
    installing the object and taking the images.

10. The method of claim 8 wherein the angular rotation of the examination arm about the first axis defines a vertical plane.

11. The method of claim 9 wherein the angular rotation of the examination arm about the first axis defines a vertical plane.

12. The method of claim 8 wherein the angular rotation of the examination arm about the first axis defines an inclined plane.

13. The method of claim 9 wherein the angular rotation of the examination arm about the first axis defines an inclined plane.

14. The method of claim 8 wherein angular rotation of the examination arm about the first axis defines a horizontal plane.

15. The method of claim 9 wherein angular rotation of the examination arm about the first axis defines a horizontal plane.

16. An apparatus for examining an object, the apparatus comprising:
    an examination arm having at one end thereof an image receiver, and a radiation delivery head at the other end; and a support on which the arm is movably mounted;

wherein the arm is mounted for rotation about a first axis and a second axis;

wherein the first axis is substantially perpendicular to the direction of the arm and passes centrally through an examination position intended for receiving the object to be examined; and wherein the second axis is substantially perpendicular to the first axis and to the examination arm, the second axis being disposed between the one end and the other end of the examination arm.

17. The apparatus of claim 16, wherein the second axis is offset from the first axis.

18. The apparatus of claim 16, wherein the arm, the first axis, and the second axis, define an orthogonal set of axis.

19. The apparatus or claim 16, wherein rotation of the arm about the first axis may result with the object to be examined remaining substantially stationary at the examination position.

20. The apparatus of claim 16, wherein rotation of the arm about the first axis, absent translational movement between the arm and the support, may result with the object to be examined remaining substantially stationary at the examination position.

* * * * *